United States Patent [19]

Morrison

[11] 4,399,078
[45] Aug. 16, 1983

[54] HYDROCARBON SOLVENT SOLUTIONS OF COMPLEXES OF N-BUTYLLITHIUM AND ETHYLLITHIUM

[75] Inventor: Robert C. Morrison, Gastonia, N.C.

[73] Assignee: Lithium Corporation of America, Bessemer City, N.C.

[21] Appl. No.: 395,272

[22] Filed: Jul. 6, 1982

Related U.S. Application Data

[63] Continuation-in-part of Ser. No. 357,843, Mar. 15, 1982, abandoned.

[51] Int. Cl.$^3$ .............................................. C07F 1/02
[52] U.S. Cl. ............................ 260/665 R; 252/431 L
[58] Field of Search ................................. 260/665 R

[56] References Cited

U.S. PATENT DOCUMENTS

| | | | |
|---|---|---|---|
| 3,082,264 | 3/1963 | West et al. | 252/431 L |
| 3,122,592 | 2/1964 | Eberly | 260/665 R |
| 3,438,420 | 4/1969 | Rai et al. | 260/665 R X |
| 3,452,111 | 6/1969 | Kamienski et al. | 252/431 L |
| 3,452,112 | 6/1969 | Kamienski et al. | 260/665 R |
| 3,751,501 | 8/1973 | Kamienski et al. | 252/431 L X |
| 3,872,177 | 3/1975 | Halasa | 260/665 R |

Primary Examiner—Helen M. S. Sneed
Attorney, Agent, or Firm—Sidney Wallenstein; Harry V. Strampel

[57] ABSTRACT

Hydrocarbon, especially aliphatic and/or cycloaliphatic hydrocarbon, solvent solutions of complexes of n-butyllithium and ethyllithium, exemplified by (a) equimolar solutions of n-butyllithium and ethyllithium in n-hexane or cyclohexane, (b) 36 molar % n-butyllithium and 64 mole % ethyllithium in n-hexane or cyclohexane, and (c) 25 mole % n-butyllithium and 75 mole % ethyllithium in n-hexane or cyclohexane. The thermal stability of the complexes of n-butyllithium and ethyllithium in the solutions thereof in hydrocarbon solvents has been found to be outstanding. The hydrocarbon solvent solutions of said complexes, especially where said solvents are aliphatic or cycloaliphatic, have marked advantages over conventionally used hydrocarbon solvent solutions of n-butyllithium as catalysts or initiators in polymerization reactions, telomerization reactions, metalation reactions, halogen-metal interchange reactions, and in the preparation of magnesium alkyls and other organometallics.

27 Claims, No Drawings

HYDROCARBON SOLVENT SOLUTIONS OF COMPLEXES OF N-BUTYLLITHIUM AND ETHYLLITHIUM

This application is a continuation-in-part of application Ser. No. 357,843, filed Mar. 15, 1982, now abandoned.

BACKGROUND OF THE INVENTION AND DESCRIPTION OF THE PRIOR ART

It has heretofore been known, as disclosed in *J. American Chemical Society*, Vol. 85, pp. 485-6 (Weiner and West, 1973), in the article entitled "Complex Formation Between Ethyllithium and t-Butyllithium", to produce complexes of ethyllithium and t-butyllithium by dissolving ethyllithium and t-butyllithium in benzene. This article points out that ethyllithium alone is sparingly soluble in cold benzene (generally speaking, ethyllithium has a solubility of 0.2 N in n-hexane and somewhat higher in cyclohexane at room temperature) but its solubility is greatly enhanced when the benzene solution contains t-butyllithium; and that the solution of the ethyllithium and the t-butyllithium forms a complex in which both the ethyl and t-butyl groups are bonded to lithium. The complexes are stated to be believed to be electron-deficient polymers of the type $(EtLi)_n(t\text{-}BuLi)_{m\text{-}n}$, where m is a small number such as 4 or 6.

The said article further points out that, when benzene from a benzene solution of ethyllithium and t-butyllithium is evaporated, a low melting white solid residue is obtained which is highly soluble in pentane, unlike ethyllithium which is virtually insoluble in pentane; that the ratio of ethyl to t-butyl groups in the resublimed complex is nearly the same as in the original benzene solution; and that 1:1 ratios, as well as 1.8:1 ratios, of the ethyllithium to the t-butyllithium produced, on distillation, distilled products with ethyl:t-butyl ratios of 1.1:1 and 1.7:1, respectively, m.p. 68°-72° C. and 56°-59° C. Benzene solutions specifically containing 8 wt% each of ethyllithium and t-butyllithium are disclosed in said article.

Finally, the aforesaid article states that it was not known whether the formation of mixed organolithium compounds will occur generally, but that preliminary results indicate that t-butyllithium enhances the solubility of phenyllithium in benzene, but only to a limited extent. No uses or utilities are disclosed or suggested for the complexes of the ethyllithium and t-butyllithium or the benzene or pentane solutions thereof; or, for that matter, of the very generally disclosed phenyllithium solutions in benzene to which t-butyllithium was added.

As is pointed out in the article by Weiner, Vogel and West entitled "The Physical Properties and Structure of t-Butyllithium", *Inorganic Chemistry*, Volume 1, No. 3, August, 1962, pure t-butyllithium is a colorless crystalline solid, readily soluble in hydrocarbon solvents. Solutions of pure t-butyllithium in refluxing n-heptane turn brown and deposit a precipitate after about an hour, indicating that noticeable decomposition occurs during this time. A comparison is referred to with ethyllithium in relation to the degree of association, and it is stated that the average degree of association of t-butyllithium is very nearly four over a considerable range of concentrations in solutions in benzene and n-hexane, whereas the average degree of association in benzene solutions for ethyllithium is about six.

It has also been known to the art to prepare complexes (a) of ethyllithium with polyisoprenyllithium, (b) of n-butyllithium with isoprenyllithium, (c) of sec-butyllithium and polyisoprenyllithium, and, generally, of corresponding complexes where polystyryllithium was used in place of polyisoprenyllithium, in liquid hydrocarbon solvents such as benzene and n-hexane, *Macromolecules*, Vol. 3, No. 3, May, June, 1970, pp, 333–337, article entitled "The Cross-Association of Polyisoprenyllithium with Ethyllithium", Morton, Patt and Fetters. These complexes have been prepared in connection with studies dealing with association phenomena in organolithium polymerizations in hydrocarbon solvents based upon the possibility of cross-association between the propagating polymer-lithium species and any residual alkyllithium initiator since this could lead to complex kinetics in both the initiation and propagation reactions. Such studies were based upon concentration solution viscosity measurements. The authors reach the conclusion that the following association equilibrium can be written for this system:

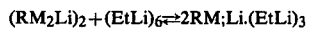

$$(RM_2Li)_2 + (EtLi)_6 \rightleftharpoons 2RM;Li.(EtLi)_3$$

and that in the polymerization reaction preferential cross-association occurs.

Furthermore, it has been known, as disclosed in U.S. Pat. No. 3,452,111, patented June 24, 1969 on an application filed Dec. 9, 1966, which patent was issued to and is owned by the Assignee (now by change of name, etc., to Lithium Corporation of America, a Delaware corporation), of the present application, that the stability against decomposition of sec-butyllithium and other heat labile secondary alkyllithiums, notably those containing from 4 to 8 carbon atoms in the alkyl radicals, generally in the form of solutions thereof in inert organic solvents, can be substantially increased by the addition thereto of variable proportions, specifically of isopropyllithium and/or n-butyllithium. This patent does not deal in any way with ethyllithium, makes no reference whatever to the enhancement of the solubility of ethyllithium in inert organic solvent solutions thereof by the addition thereto of sec-butyllithium (or, for that matter, by the addition thereto of n-butyllithium or of isopropyllithium), or to the enhancement of the stability of sec-butyllithium or n-butyllithium or isopropyllithium by the addition thereto or the admixture therewith of ethyllithium, and said patent never contemplated the discoveries to which the present invention is directed.

It has also heretofore long been known and disclosed in numerous patents in connection with the preparation of homopolymers as well as copolymers of butadienes such as 1,3-butadiene; isoprene; vinyl-substituted hydrocarbons; vinyl halides; vinylidene halides; esters of acrylic acid; esters of homologs of acrylic acid, and numerous other polymerizable monomers; as well as in the preparation of telomers, to utilize, as catalysts or initiators in such polymerization and telomerization reactions, metallic lithium; lithium hydrocarbons; alkyllithiums corresponding to the formula $R(Li)_x$ where R is a saturated or unsaturated hydrocarbon radical selected from the group consisting of aliphatic, cycloaliphatic, aralkyl, alkaryl, and aromatic radicals, and x is an integer from 1 to 4, inclusive, and wherein the R group has a valence equal to the integer x and preferably contains from 1 to 20 carbon atoms. Examples thereof are methyllithium, ethyllithium, isopropyllithium, n-butyllithium, amyllithium, hexyllithium, t-octyllithium, cyclohexyllithium, s-butyllithium, t-butyllithium, and t-amyllithium, phenyllithium, tolyllithiums, xylyllithiums, alpha-and beta-naphthyllithiums, allyllithium, methallyllithium; hydrocarbon polylithium compounds such as methylene dilithium, ethylene dilithium, trimethylene dilithium, octadecamethylene dilithium, and 1,2-dilithium propane; polylithium aryl, aralkyl and alkaryl compounds such as 1,4-dilithium benzene, 1,5-dilithium naphthalene, 1,2-dilithium-1,3-diphenyl propane; tri and higher lithium hydrocarbons such as 1,3,5-trilithium pentane and 1,3,5-trilithium benzene.

The foregoing organolithium compounds are disclosed in, among other patents, U.S. Pat. Nos. 2,975,160; 3,065,218; 3,094,512; 3,231,635; 3,294,768; 3,297,793; 3,301,840; 3,317,918; 3,324,191; 3,332,856; 3,427,364; 3,449,306; 3,464,961; 3,465,065; 3,498,960; 3,513,056; 3,554,911; 3,558,575; 3,607,846; 3,652,516; 3,692,874; 3,742,077; 3,752,501; 3,760,025; 3,787,377; 3,840,616; 4,057,601; 4,076,914; and 4,237,245; Canadian Patent No. 750,006; and Australian Pat. No. 262,782. The general statement is made in some of these patents, after listing many of the aforesaid organolithium compounds, including unsaturated organolithium compounds and aryl, aralkyl and alkaryl lithium compounds such as allyllithium, methallyllithium, phenyllithium, tolyllithiums, xylyllithiums and naphthyllithiums, that mixtures of such organolithium compounds can be used, but no particular examples of any such mixtures are given. Illustrative of such patents are U.S. Pat. Nos. 3,506,631 and 3,632,563; and British Pat. Nos. 817,693; 817,695; and 994,726. None of these patents provides any concept or teachings which would lead one versed in the art to my present invention and the important benefits which result therefrom.

With due regard for the foregoing disclosures in the above-enumerated patents concerning the uses, as catalysts or initiators of any of large numbers of different organolithium compounds in polymerization and other reactions, or, as noted above, very generally stated mixtures of such organolithium compounds, it will be seen from said patents that, in practically all of them, in the actual disclosed working examples, with very minor exceptions, n-butyllithium is the catalyst or initiator of choice. This is because it has been found to be, with very limited exceptions, the most desirable organolithium compound from the overall standpoints of its effectiveness utility-wise for the intended reactions, its relative ease of handling, manufacture and for other reasons as well.

BRIEF DESCRIPTION OF THE PRESENT INVENTION

In connection with considerable investigatory work which I have conducted and have had conducted, it has been found that the behavior and properties of mixed alkyllithiums in hydrocarbon solvents, for instance, aliphatic or cycloaliphatic liquid hydrocarbon solvents, is unpredictable. Thus, in the case of methyllithium, I have found that, for instance, whereas the complexes of n-butyllithium with ethyllithium of the present invention can highly effectively be prepared by the methods described below in the illustrative general procedure and working Examples of this specification, such procedures and methods are ineffective or essentially or practically inoperative for the preparation of complexes of t-butyllithium and methyllithium or complexes of n-butyllithium and methyllithium, nor by the mixing of independently-prepared t-butyllithium or independently-prepared n-butyllithium with independently-prepared methyllithium in liquid hydrocarbon solvents illustrative of which are n-hexane or cyclohexane.

I have discovered, among other things, that n-butyllithium forms complexes with ethyllithium which have important advantages over n-butyllithium alone or ethyllithium alone, or over solutions thereof in liquid hydrocarbon solvents, particularly aliphatic and/or cycloaliphatic hydrocarbon solvents, such as hexane or cyclohexane, as well as in their usefulness as catalysts or initiators in polymerization and other reactions. I have discovered that the addition of n-butyllithium results in materially increasing the solubility of ethyllithium in said solvents, exemplified particularly by hexane and cyclohexane. I have further discovered that, for instance, under certain conditions and circumstances, the complexes which result from such mixtures of n-butyllithium and ethyllithium, when dissolved in hydrocarbon solvents, notably n-hexane and/or cyclohexane, have exceptional and unexpected thermal stability, being very materially more thermally stable than n-butyllithium, depending on the mole ratios of the n-butyllithium to the ethyllithium, and also depending on the concentrations of the complexes of the n-butyllithium and ethyllithium and also being, to some extent, in certain instances, influenced by the particular hydrocarbon solvents in which said novel complexes are dissolved. Such thermal stability tests have been carried out at a temperature of 40° C. and for time periods of 111 and 119 days and longer periods. In the case of complexes of equimolar proportions of n-butyllithium and ethyllithium, and of 25 mole % n-butyllithium and 75 mole % ethyllithium in dilute solutions in n-hexane or cyclohexane, no loss of activity occurred at the end of ~4 months, as against a loss of the order of about 4.5 to about 5% or more in solutions of the same concentration of n-butyllithium alone.

It has been discovered by me that the stability of the complexes of n-butyllithium and ethyllithium is pronouncedly greater, at various temperatures, illustratively at about 40° C., when such complexes are in the form of dilute solutions in liquid hydrocarbon solvents, illustratively, hexane or cyclohexane or mixtures thereof. Such dilute solutions may vary in their content of said complexes but, generally speaking, it is advantageous to market them in the form of solutions containing from about 12 to about 25 wt.%, or from about 12 to about 40 wt.% of said complexes, particularly about 15 to about 25 wt.%. Thus, by way of illustration, as has been indicated above, dilute solutions of complexes of equimolar proportions of n-butyllithium and ethyllithium, and of complexes of 25 mole % n-butyllithium and 75 mole % ethyllithium in n-hexane demonstrated exceptional thermal stability, losing no C-Li activity after ~4 months at 40° C. For the purposes of the present invention, dilute solution may be considered as containing less than 40 wt.% of the complexes, and particularly advantageous, from a stability standpoint, being those containing from about 12 or 15 to about 25 wt.% of said complexes. Indeed, solutions containing of the order of about 15 to about 25 wt.% of equimolar proportions of n-butyllithium and ethyllithium, in hexane or cyclohexane, appear to be thermally stable indefinitely in sealed containers up to 40° C.

In this same vein, concentrated solutions may be considered as containing at least 40 wt.% of the complexes, for instance, from about 40 to about 72 wt.% of the complexes, and more commonly those containing from about 65 to about 95 weight % of the complexes, indeed as high as 99 wt.% as noted below, depending upon the solubility of the particular complexes in given hydrocarbon solvents, while still maintaining substantial clarity of the solutions of said complexes. The solubility of the complexes is dependent also upon the mole percentages of the n-butyllithium and ethyllithium of the particular complex and, as indicated above, upon the particular hydrocarbon solvent used. Thus, simply by way of illustration, where a complex of equimolar proportions by weight of the n-butyllithium and ethyllithium is initially prepared containing, say, 15 or 25 or under 40 wt.% of said complex dissolved in hexane or cyclohexane, such can be concentrated by evaporating off hexane to such an extent that the resulting concentrate contains at least about 99 wt.% of said complex (or 13.6 wt.% active lithium) in the form of a clear solution. In comparison to the commercially available concentrated 90 wt.% n-butyllithium, which contains 9.8 wt.% active lithium, a 90 wt.% concentrate of an equimolar n-butyllithium-ethyllithium complex contains 12.49 wt.% active lithium. Thus, this complex advantageously provides a product which contains more lithium due to the lower molecular weight of the complex.

In liquid hydrocarbon solutions containing increasing proportions of the complexes of the present invention, notably highly concentrated solutions of said complexes, the extent of the enhancement of the thermal stability of the complexes of the present invention, in comparison with the thermal stability of similarly concentrated solutions of n-butyllithium, is substantially reduced. Thus, tests of thermal stability of concentrated solutions, in hexane, of complexes of equimolar proportions of n-butyllithium and ethyllithium (63.6 wt.% RLi—8.83 wt.% Li) showed that said solutions were just slightly more stable than concentrated solutions, in hexane, of n-butyllithium alone (87.4 wt.% RLi—9.47 wt.% Li), in which case each sample contained similar amounts of lithium. At 40° C., the concentrated solution of the complex lost 0.17% RLi/day, whereas the concentrated solution of the n-butyllithium alone lost 0.22% RLi/day. At still higher levels of lithium content, an equimolar complex of n-butyllithium and ethyllithium (92.8 wt.% RLi—12.88 wt.% Li) lost 0.26% RLi/day.

As indicated above, thermal stability tests were also carried out on liquid hydrocarbon solutions of different concentrations of n-butyllithium alone, at the illustrative temperature of 40° C. Furthermore, although, as previously stated, ethyllithium is very sparingly soluble in such liquid hydrocarbons as hexane and cyclohexane, thermal stability tests were conducted on a comparatively dilute, yet saturated, solution (about 0.4 N) of ethyllithium in cyclohexane, as noted below. So far as I am aware, prior to my present invention, no thermal stability data have been reported in the previous literature in regard to ethyllithium in solution. A knowledge of its thermal stability properties is important because the complexes of the present invention generally, and especially advantageously, contain at least about 50 mole % of ethyllithium. Prior to my present invention, ethyllithium, while per se being well known to the art, had essentially no commercial value because, apart from other considerations, of its very low solubility in liquid hydrocarbon solvents, as well as a relatively minimal knowledge concerning the scope of other alkyllithiums substantially to enhance its solubility in liquid hydrocarbon solvents, and a lack of knowledge by the prior art of the effect on the thermal stability of the complexes which might be formed between ethyllithium and other particular alkyllithiums.

Additional data in regard to thermal stability are reflected by the tests shown by the following Tables.

TABLE I

Comparison of Thermal Stability of Concentrated Solutions in Hexane of n-butyllithium alone and of a Complex of Equimolar Proportions of n-butyllithium and ethyllithium at 40° C.

| | Alkyllithium | Active RLi (wt. %) | Active Li (wt. %) | Total Loss of Activity (%) | Days | % Loss/Day |
|---|---|---|---|---|---|---|
| I | n-butyllithium | 87.4 | 9.47 | 19.6 | 89 | 0.22 |
| II | Equimolar Complex of n-butyllithium and ethyllithium | 63.6 | 8.83 | 14.3 | 85 | 0.17 |
| III | Equimolar Complex of n-butyllithium and ethyllithium | 92.8 | 12.88 | 12.5 | 47 | 0.26 |

The above data indicate that the complex in II is slightly more thermally stable than the n-butyllithium alone (I) if compared on the same lithium content basis. However, the thermal stability of the complex in the solution containing appreciably more active lithium (36%) (III) is slightly less than that of the n-butyllithium alone (I).

TABLE II

Thermal Stability of Concentrated n-butyllithium in Hexane at 40° C. Storage

| Days | Total Base (wt. %) | $V_2O_5$ (wt. %) | Loss of Active RLi (%) |
|---|---|---|---|
| 0[1] | 89.7 | 87.4 | 0 |
| 16 | 89.0 | 83.2 | 4.8 |
| 65[2] | 88.1 | 74.2 | 15.1 |
| 89[2] | 87.0 | 70.3 | 19.6 |

[1]Sample hazy
[2]Sample turbid

TABLE III

Thermal Stability of Concentrated Equimolar Complex of n-butyllithium and ethyllithium[1] at 40° C. Storage

| Days | Total Base (wt. %) | $V_2O_5$ (wt. %) | Loss of Active RLi (%) |
|---|---|---|---|
| 0[2] | 68.0 | 63.6 | 0 |
| 16 | 66.3 | 60.7 | 4.6 |
| 85[3] | 61.9 | 54.5 | 14.3 |

[1]Initial concentration of complex = 63.6 wt. %.
[2]Sample clear
[3]Sample turbid

TABLE IV

Thermal Stability of
Concentrated Equimolar Complex of
n-butyllithium and ethyllithium[1]
at 40° C. Storage

| Days | Total Base (wt. %) | $V_2O_5$ (wt. %) | Loss of Active RLi (%) |
|---|---|---|---|
| 0[2] | 94.5 | 92.8 | 0 |
| 11 | 95.5 | 92.5 | 0.3 |
| 39 | 95.5 | 83.9 | 9.6 |
| 47[3] | 93.1 | 81.2 | 12.5 |

[1]Initial concentration of NBEL 50:50 = 92.8 wt. %.
[2]Sample clear
[3]Sample turbid

TABLE V

Thermal Stability of
ethyllithium in Cyclohexane
at 40° C.

| Days | Total Base (N) | $V_2O_5$ (N) | Loss of Active RLi (%) |
|---|---|---|---|
| 0[1] | 0.44 | 0.41 | 0 |
| 22 | 0.41 | 0.40 | 2.4 |
| 64 | 0.44 | 0.41 | 0 |
| 114 | N.A. | 0.39 | 4.9 |

[1]Sample clear

I have also found that complexes of equimolar amounts of n-butyllithium and ethyllithium in various hydrocarbon solvents as, for example, n-hexane or cyclohexane, can be concentrated by careful evaporation to produce clear concentrates of said complexes up to 90 wt. % or even higher with no precipitation. Preparation of such n-butyllithium and ethyllithium complexes, in the form of clear solutions of n-hexane, containing higher mole percentages of ethyllithium, indicated that 1 n-butyllithium is needed to solubilize 5 ethyllithium (hexamer). The concentrations of these solutions were ~1.0 N. Attempts to incorporate more ethyllithium result in an insoluble product left on the filter. When ethyllithium is also prepared directly from ethyl chloride and a lithium dispersion, the resultant ethyllithium crystals can be dissolved and complexed with n-butyllithium in the same ratio (n-butyllithium/5 ethyllithium) as described above.

The relative proportions of the n-butyllithium and the ethyllithium are variable within reasonable limits, generally in a molar ratio of 10:90 n-butyllithium to 90:10 ethyllithium while maintaining solubility in the liquid hydrocarbon solvent. Thus, for example, equimolar amounts of n-butyllithium and ethyllithium are fully soluble in n-hexane. Relative mole proportions of 25 n-butyllithium and 75 ethyllithium are soluble to an extent to produce in the range of about 20 to about 25 wt. % in n-hexane. Relative mole proportions of 17 n-butyllithium and 83 ethyllithium are soluble to an extent to produce in the range of about 5 to 10 wt. % solutions in n-hexane. In general, it is especially advantageous to utilize mixtures of n-butyllithium and ethyllithium, in solutions of the aforesaid hydrocarbon solvents, in which the mole ratio of the n-butyllithium to the ethyllithium is 50:50, or in the mole ratio of about 35 n-butyllithium to about 65 ethyllithium. Equimolar proportions of n-butyllithium and ethyllithium can produce clear solutions containing as high as about 98 wt. % of such complexes at room temperature in n-hexane or cyclohexane if one desires such highly-concentrated solutions. Complexes in which the mole ratio of n-butyllithium to ethyllithium is 36:64 can produce clear solutions having concentrations as high as approximately 72% at room temperature. Complexes in which the mole ratio of the n-butyllithium to ethyllithium is 25:75 can produce clear solutions having concentrations as high as approximately 23 wt. % in n-hexane and as high as about 25 wt. % in cyclohexane. Complexes containing as low as about 10 mole % n-butyllithium, balance with 90 mole % ethyllithium, in some of said liquid hydrocarbon solvents can be obtained.

As indicated above, the complexes of the n-butyllithium and the ethyllithium, particularly in solution in aliphatic and/or cycloaliphatic hydrocarbon solvents, are highly useful, and at substantial economical advantages, as has been indicated above, in various reactions where n-butyllithium solutions in such solvents have been used, such as initiator/catalysts for stereospecific polymerization of conjugated dienes, such as butadiene and isoprene, and for copolymerization of dienes with vinyl aromatic compounds such as styrene, such as are disclosed in the patents listed above, and wherein, in certain of such polymerization reactions, the polymerization reactions proceed more rapidly than when ethyllithium alone or n-butyllithium alone is used as a catalyst or initiator; as well as for use as cocatalysts for low pressure (Ziegler) polymerization of α-olefins; as well as in other reactions such as metalation reactions in which hydrogen is replaced by lithium; in halogen-metal interchange reactions; metalation of substrates to form carbanion intermediates; and in the preparation of magnesium alkyls such as are disclosed in U.S. Pat. Nos. 3,646,231 and 3,755,478.

While n-hexane and cyclohexane represent the liquid hydrocarbon, particularly the aliphatic and cycloaliphatic hydrocarbon, solvents of choice in which the complexes of n-butyllithium and ethyllithium of the present invention are used, and are prepared for use, various other inert aliphatic or aromatic hydrocarbon solvents or mixtures thereof which can be used, although generally less preferred, which will usually contain from 5 to 12 carbon atoms, are n-pentane, 2,4-dimethylhexane, octane, isooctane, n-decane, n-dodecane, methylcyclohexane, benzene, toluene, n-propyl benzene, isopropylbenzene, xylenes, and the like. Mixtures of such liquid hydrocarbons can be employed as, for example, mixtures of n-hexane and cyclohexane in variable proportions to each other such as 50—50 mixtures, 75-25 mixtures, 60-40 mixtures, etc. Generally speaking, however, it is more desirable to use a single liquid hydrocarbon solvent since no particular advantage is generally achieved by using mixtures thereof.

From a manufacturing standpoint, the n-butyllithium/ethyllithium complexes, dissolved in aliphatic and/or cycloaliphatic hydrocarbon solvents, have the further advantage over n-butyllithium by reason of the fact that they possess an overall lower molecular weight than n-butyllithium which results in increasing the capacity of an installation since the capacity of any installation increases inversely proportionally to the molecular weight of the mixture constituting the n-butyllithium/ethyllithium complex contrastingly to the higher molecular weight of the n-butyllithium.

In the preparation of the complexes of n-butyllithium and ethyllithium in accordance with my present invention, it has been found to be especially satisfactory to prepare them directly by reacting a premixture of n-butyl chloride or bromide and ethyl chloride or bromide, most desirably in the form of a relatively homogeneous premixture, with a stirred dispersion or slurry of finely divided lithium metal in a liquid hydrocarbon, particularly of aliphatic or cycloaliphatic character, such as n-hexane or cyclohexane, in which the complexes produced are soluble, said reaction being advantageously carried out at a temperature in the range of about 25° to about 35° C. It is particularly desirable that the reaction be initiated by initially adding to the stirred lithium metal dispersion or slurry a small amount, usually not more than about what is equivalent to about 2% of the total of the premixture of the n-butyl chloride or bromide and the ethyl chloride or bromide, after which the said premixture is added gradually, under conditions of relatively vigorous stirring, until the reaction for producing said complexes is completed. The stirring is then discontinued and the unused or excess lithium metal is allowed to rise to the top of the reaction mass from where it is then drawn off. The "muds" which form during the reaction, consisting primarily or essentially of lithium chloride (or lithium bromide if n-butyl bromide and ethyl bromide are utilized), are separated from the liquid of the reacted mass, desirably by filtering, and said muds are washed one or more times with a given volume of the liquid hydrocarbon solvent, to recover from said muds the complexes adhering thereto or carried thereby. The washings may be added to the prior filtrate comprising the clear solution of the complexes in the liquid hydrocarbon solvent.

Alternatively, in the carrying out of the above-described method, instead of allowing the lithium metal to rise to the surface and be drawn off after the completion of the reaction to produce the complexes and then separately separating the muds, as by filtration, the entire mass including the lithium metal and the muds are filtered off and separated from the filtrate comprising the solution of the complexes in the hydrocarbon solvent, and the separated solids are washed with the hydrocarbon solvent to recover the complexes carried by the separated solids.

As noted above, a homogeneous premixture of n-butyl chloride and ethyl chloride, in the selected predetermined proportions, is added to the lithium metal slurry in the carrying out of the reaction to produce the desired complexes of the n-butyllithium and ethyllithium. Instead of so proceeding, one may gradually feed simultaneously, separately, into the lithium metal slurry, the n-butyl chloride and the ethyl chloride, at rates so as to correspond to the desired selected predetermined proportions to produce the particular complexes of the n-butyllithium and ethyllithium. This approach, however, is distinctly less desirable and not preferred for a variety of reasons including handling difficulties as well as possessing other disadvantages.

No novelty is claimed per se in the preparation of the lithium metal dispersion proper in the hydrocarbon solvent. This is conveniently done by vigorous stirring or admixing finely divided lithium metal in an inert liquid medium, most desirably a mineral oil, illustratively a mineral oil such as that sold under the trade designation PRIMOL 155, or an admixture thereof with petrolatum, for instance, in proportions of about 25 to about 35 wt. % of the lithium metal, balance mineral oil or mineral oil admixed with some petrolatum. Mineral oil, alone, as the dispersing agent for the finely divided lithium metal is preferred. The lithium metal advantageously is admixed with or is made so as to contain a small percentage of sodium metal, e.g., 0.5 to 2%, preferably about 0.7% to about 1.7%, which serves to enhance the formation of the n-butyllithium and the ethyllithium complexes. To some extent, small proportions of other metals can be used in place of or in conjunction with sodium as, for example, potassium, rubidium, cesium or calcium, but sodium metal is especially useful. No novelty, however, is claimed per se broadly in using lithium metal admixed with a small proportion of sodium metal (and/or said other metals) in reactions with an alkyl halide to produce an alkyllithium since this is, in itself, known to the art. When reference is made to lithium metal in lithium metal dispersions, it will be understood to mean lithium metal containing or admixed with a small proportion, e.g., of the order of at least about 0.5% and up to about 2% more or less of sodium metal (and/or generally equivalent metal). The foregoing generally known procedural aspects are shown in various of the above-mentioned patents as well as in U.S. Pat. No. 3,452,112 of which I am one of the joint inventors. All operations, to the extent reasonably feasible, are carried out under inert gas conditions or in an inert gas atmosphere, such as argon or helium, since, as is well known to the art, air, oxygen and moisture are detrimental to reactions of the type disclosed in the present invention and the presence thereof is to be avoided to the maximum extent reasonably possible.

In the practice of the method of the present invention for the preparation of the novel complexes of n-butyllithium and ethyllithium, high yields of said complexes are commonly obtained, generally of the order of about 88 to about 95%. Thus, by utilizing the foregoing novel procedure, clear solutions of complexes of n-butyllithium and ethyllithium are directly formed in the particularly desired aliphatic or cycloaliphatic liquid hydrocarbon solvents, whereas, if the n-butyl chloride or bromide and the ethyl chloride or bromide are similarly reacted separately in the manner otherwise described, the aforesaid hydrocarbon-soluble n-butyllithium and the aforesaid hydrocarbon-insoluble ethyllithium, respectively, would be formed which is most unsatisfactory and would cause severe handling and manipulative problems.

Furthermore, by carrying out the production of the aforesaid n-butyllithium and ethyllithium complexes in the novel and advantageous manner described above, the additional important advantage is achieved of rendering unnecessary the use of strong Lewis Bases, e.g., ethers. In fact, and of definite significance, the simultaneously formed soluble species n-butyllithium apparent solubilizes the insoluble species ethyllithium as it forms, thereby keeping the lithium metal surface clean and allows the reaction rapidly to proceed to completion, without complications. The preparation of the complexes of n-butyllithium and ethyllithium in accordance with the present invention has the still further advantage that, due to the lower molecular weight of said complexes, as compared to that of n-butyllithium, more C-Li equivalents/lb per batch is obtained which, as generally noted above, results in an increase of plant capacity per unit of time. In this connection, by way of more specific illustration, the increase of throughput or plant capacity on a mole basis for the production of an equimolar proportion complex of n-butyllithium and ethyllithium is about 28% greater than in the case of the production of n-butyllithium alone; and, in the production of a complex containing 25 mole % of n-butyllithium and 75 mole % of ethyllithium, said increase is about 49% greater than in the case of the production of n-butyllithium alone.

The following examples are illustrative of the preparation of the complexes of n-butyllithium and ethyllithium made in accordance with the present invention. An illustrative general procedure will first be described followed by specific examples. It will be understood that these examples are in no way limitative of my invention since various changes may be made in proportions of reactants and other ingredients, temperatures and times at which the reactions are carried out, and in other respects in light of the guiding principles and teachings disclosed herein. In said illustrative procedure and in said example, the following described apparatus or equipment set-up was employed. It will, of course, be understood that this is simply exemplary and those skilled in the art can readily evolve modified apparatus set-ups particularly in connection with scale-up operations for large or commercial plant production of the complexes. All temperatures recited are in °C.; and all percentages referred to are in terms of molar percentages unless otherwise expressly stated. For convenience, n-butyllithium will sometimes hereinafter be referred to as NBL; ethyllithium will be referred to as EL; and the complexes of n-butyllithium and ethyllithium will be referred to as NBEL.

Apparatus 250 ml round bottom reaction flask (3 neck)
Dry-ice condenser
250 ml jacketed dropping funnel (CO$_2$-hexane cooled)
Thermometer (0° to 100° C.)
Mechanical stirrer
Cooling bath (CO$_2$-hexane)
250 ml glass filter funnel (medium porosity)
500 ml round bottom receiving flask (3 neck)

Note: All glassware was baked in an oven at 150° C. for at least 12 hours prior to use. The apparatus was then set-up hot and cooled with an argon purge. The use of argon is particularly advantageous for the halogen-metal reaction; whereas, nitrogen can be used for the filtration.

Materials Used (except as specifically otherwise stated in the examples)

13.4 ml Ethylchloride (EtCl) (0.1875 moles)
6.5 ml n-Butylchloride (n-BuCl) (0.0625 moles)
13.0 gm Lithium dispersion in petrolatum and Primol 155 (30 wt. %-0.56 g. atoms)
200 ml n-Hexane (solvent)
80 ml n-Hexane (dispersion wash)
5 ml n-Butyllithium (n-BuLi) in hexane (14.8 wt. %-7.8 meq)—Li metal conditioner Illustrative General Procedure Preparation of NBEL from Premixed n-BuCl (or Br) and EtCl (or Br)

NBEL is prepared by reacting a premixture of n-BuCl and EtCl and a dispersion of finely divided lithium metal in a liquid hydrocarbon such as n-hexane or cyclohexane at a temperature of approximately 25° to approximately 35°. The chemistry is reflected by the following:

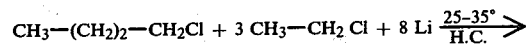

-continued

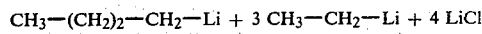

NBEL

A premixture of n-BuCl and EtCl, in predetermined mole proportions in relation to each other, as described above, is added to a vigorously stirred dispersion of finely divided metallic lithium in a hydrocarbon solvent under an inert gas atmosphere. To insure high yields of the NBEL, an excess of the lithium metal dispersion is used, for instance, of the order of about 10% to about 15%, said excess being based upon the excess stoichiometric amount of the lithium metal in relation to the premixture of the n-BuCl and EtCl. The lithium metal used in the dispersion contains, or is admixed with, as a part of the dispersion, in a small amount, based on the weight of the lithium metal, of sodium metal, generally in the amount indicated above in the specification. Prior to the carrying out of the reaction to produce the NBEL, the lithium metal is conditioned or activated by stirring into the dispersion a small proportion of previously produced NBEL, which corresponds to about 1 mole % of the total charge of the premixture of the n-BuCl and EtCl, for a period of time which is variable but which may be of the order of about an hour. The exothermic alkylhalide-metal reaction is initiated at once by the addition of 2% of the total halide charge. On heat being noted, the remaining premixture of the n-BuCl and EtCl is added gradually or dropwise at a rate necessary to keep the reaction mass temperature preferably at about 30°. The reaction is highly exothermic and cooling is generally necessary. After reaction and, desirably, a postreaction period of time, of the variable order of a half hour or more, the NBEL solution is separated from the muds (LiCl and excess Li) by filtration and the muds are washed with the same inert solvent in which the complex was prepared. NBEL is analyzed by total base (LiOH) and vanadium pentoxide (active C-Li) assays. Recovered yields are determined by the following method:

$$\text{Volume (liter)} \times \text{N} \cdot (V_2O_5) = \text{eq. C-Li}$$

$$\frac{\text{eq. C-Li}}{\text{moles halide}} \times 100 = \% \text{ Yield}$$

EXAMPLE 1

13 g of a finely divided lithium metal in petrolatum-Primol 155 and 80 ml dry n-hexane are charged with the assembled and argon purged apparatus. The resulting slurry is stirred for 15 minutes and stirring is then stopped. The lithium is allowed to rise to the top of the solution. The 80 ml of n-hexane wash containing the oil and petrolatum is then removed by syringe from the bottom of the flask. This is replaced by the reaction solvent (150 ml dry n-hexane). The jacketed dropping funnel is cooled with the dry-ice n-hexane mixture. Then the 13.4 ml of gaseous EtCl is condensed into the funnel. Next, the 6.5 ml BuCl is added to the contents of the dropping funnel. The resulting mixture is shaken vigorously to insure complete mixing. The reaction is initiated by adding ~1 ml of the mixed halides to the stirred lithium slurry. An immediate rise in temperature (3°) indicates spontaneous initiation. Addition of another 1 ml of the mixed halides solution brings the pot temperature to 30°. The dry-ice hexane cooling bath is then set in place. The n-BuCl-EtCl premixture is added dropwise over a period of about 44 minutes. The reaction is very sensitive to the halide addition but is controlled easily by the cooling bath ($\Delta T=10°$ to 15°). The resultant reaction mass is slowly stirred overnight. Filtration of the final product and a 50 ml hexane wash of the muds requires about 2 minutes. A volume of 235 ml of a clear, colorless solution of NBEL is recovered.

Analysis

Total Base = 1.03 N
Active Alkyl ($V_2O_5$) = 1.00 N
Yield = 94% (recovered)

The following additional examples, Table VI, show other runs made for the preparation of NBEL solutions in n-hexane using other mole ratios of n-BuCl-EtCl. In these examples, a refluxing hydrocarbon solvent mixture of n-butane (B.P.-0.5°) and n-hexane at about 30° is the reaction medium. The excellent yields are due at least in part because of efficient heat transfer caused by the vaporization of the n-butane at the site of reaction, namely, the lithium-metal surface. Efficient removal of the intense heat of reaction all but eliminates the competing reaction of Wurtz coupling. In NBEL preparations in the absence of butane, the presence of volatile ethyl chloride (B.P. 13.1° C.) possibly may also be responsible for the same beneficial heat transfer. Although very little condensation is noted in the condenser, immediate fogging appears above the reaction slurry upon the addition of the mixed halides. The NBEL obtained from the above examples is crystal clear after filtration.

as to the manner in which the tests with respect thereto were carried out is believed to be in order. Because of the known readiness with which alkyllithiums degrade due to their high rate of reaction to $O_2$ and $H_2O$ with the resulting lowering of their C-Li activity, as well as causing other problems, the thermal stability tests reported herein of NBEL solutions in liquid hydrocarbon solvents were carried out in a manner such as to minimize contact with $O_2$ and $H_2O$ and to obtain a distinctly more accurate picture of the true thermal stability properties of said NBEL solutions. Thermal decomposition of alkyllithiums proceeds by lithium hydride elimination:

$$RLi \rightarrow Olefin + LiH$$

The matter of thermal stability of alkyllithiums is highly important because the rate of thermal degradation dictates the way alkyllithiums must be handled, stored and shipped.

Thermal stability of alkyllithium is commonly carried out by placing samples thereof in rolled steel cylinders (30 and 55 in.$^3$ volume). Prior to use, each cylinder is equipped with the appropriate fittings to insure a leak proof system and then is "pickled" or conditioned with the alkyllithium. The alkyllithium solution in the hydrocarbon solvent is then placed in the cylinder and analyzed for total base and active RLi ($V_2O_5$ method). The sample is then placed in a constant temperature bath at 40° C. ($\pm 1°$ C.). Periodically, the cylinder is removed from the bath, opened and reanalyzed for total base and active RLi. From these data, the thermal stability of the

TABLE VI

| | | | Preparation of NBEL in n-Hexane | | | | | | |
|---|---|---|---|---|---|---|---|---|---|
| | | Butyl | Lithium Metal | | | | Analysis | | Recovered |
| Ex. No. | n-BuCl Moles | EtCl (Moles) | Ethyl (Ratio) | gm (Atoms) | % (Excess) | n-Hexane ml | n-BuLi[1] (Moles) | Total Base (N) | Active Alkyl (N) | Yield (%) |
| 2 | 0.125 | 0.125 | 1:1 | 0.58 | 14 | 150 | 0.007 | 1.33 | 1.30 | 95.0 |
| 3 | 0.025 | 0.225 | 1:9 | 0.58 | 14 | 150 | 0.007 | 1.02 | 0.98 | 100.0 |
| 4 | 0.245 | 0.207 | .17:83 | 0.58 | 14 | 150 | 0.007 | 0.99 | N.A. | 92.1 |

[1] Amount of n-butyllithium used to condition or activate the lithium dispersion.

In the following Table VII, illustrative examples are shown of the preparation of NBEL solutions in cyclohexane, as well as in hexane.

alkyllithium is calculated and plotted on graph paper (% loss active RLi vs. time). Since the cylinder is opened and sampled several times during the course of

TABLE VII

| | | | Preparation of NBEL in Cyclohexane | | | | | | | |
|---|---|---|---|---|---|---|---|---|---|---|
| | | n-Butyl- | Lithium Dispersion | | Reaction Solvent | | Metal Conditioner[1] | | Analysis | | Recovered |
| Ex. No. | n-BuCl (Moles) | EtCl (Moles) | Ethyl (Mole Ratio) | gm (Atoms) | % (Excess) | (Type) | (ml) | (Type) | (Moles) | Total Base (N) | Active Alkyl (N) | Yield (%) |
| 5 | 0.50 | 0.50 | 1:1 | 2.2 | 10 | Cyclohexane | 250 | n-BuLi | 0.008 | 1.79 | N.A. | 99.4 |
| 6 | 0.25 | 0.25 | 1:1 | 1.1 | 10 | Cyclohexane | 250 | n-BuLi | 0.008 | 0.96 | 0.93 | 98.0 |
| 7 | 0.375 | 0.125 | 75:25 | 1.1 | 10 | Hexane | 250 | n-BuLi | 0.008 | 1.86 | 1.73 | 98.0 |

[1] The amount of n-BuLi used to condition the lithium dispersion prior to reaction.

The runs of Examples 5 and 6 initiate well and are sensitive to the halide feed throughout the entire addition. Filtrations are rapid, yielding light yellow, clear solutions. The final product obtained from Example 6 is concentrated to 94 wt. % (Total Base) via vacuum on a Rinco Flask Evaporator. The active alkyl analysis by $V_2O_5$ is 90.7 wt. % (Active C-li = 96.5%). The concentrate is a liquid and, at $-25°$ C., the viscosity increases but does not cause any crystallization.

With respect to the above-discussed thermal stbility of the NBEL hydrocarbon solutions, a brief explanation the test, the chance for atmospheric oxygen and $H_2O$ contamination is great. This contamination can often result in erroneously high thermal stability data because the loss due to contamination is additive to the degradative data. In addition, lithium alkoxide formed by the reaction of $O_2$ with alkyllithium increases the rate of the thermal degradation of organolithium. In the present case, all thermal stability procedure tests were carried out by a modification of the above-described method whereby the contamination problem described above was at least largely circumvented. This was done by using several cylinders of the NBEL hydrocarbon solutions to be tested. The tests were carried out as described above except that each cylinder was sampled only once. This procedure materially reduced the chance for atmospheric contamination, thus providing a more accurate thermal stability evaluation.

The following examples are illustrative of polymerization, telomerization and other reactions which are effectively carried out by the utilization of complexes of n-butyllithium and ethyllithium in liquid hydrocarbon solutions made in accordance with the present invention.

The hydrocarbon solutions of the complexes of n-butyllithium and ethyllithium of the present invention can, in general, be used in place of solutions of n-butyllithium in known polymerization and copolymerization reactions to produce liquid as well as solid polymers and copolymers, oligomers, triblock polymers, "Star" polymers, metalation and other reactions. The following examples are illustrative of such usage. All temperatures cited are in °C.

EXAMPLE A

Preparation of Polystyrene.

To an oven-dried one pint sample bottle, purged with $N_2$, is added 150 ml of dry cyclohexane. The bottle is then capped with a septum. Using a syringe, 16.5 ml of freshly distilled styrene (inhibitor free) is added to the cyclohexane. Next, the reaction vessel is placed in a constant temperature bath at 36.5° C. and continuously mixed using a shaker. 0.001 mole of the solution of the complex made in accordance with Example 2 is then added via syringe, followed by sealing of the septum with parafilm. A pale yellow color appears in a few seconds after said addition. The color of the solution becomes orange in approximately 30 seconds. The color intensity gradually increases with time and becomes a deep red after 12 hours. The polymerization is terminated after 24 hours with 2 ml of degassed isopropanol. A one ml sample of the resulting colorless solution is concentrated using a gentle $N_2$ purge. The resulting colorless film of polystyrene is then submitted to GPC analysis for determination of $M_n$, $M_w$, $M_z$ and corresponding molecular weight distributions (MWD). Based on the calculated MWD's of the polystyrenes obtained using the above procedure, the NBEL initiators produced a slightly narrower polydispersity of 1.4 compared to that of NBL which was 1.5. As a check for the procedure above, sec-butyllithium was also tested in the same manner and a MWD of 1.05 was obtained. This MWD for sec-butyllithium is in agreement with existing data for this more reactive initiator.

EXAMPLE B

Preparation of Telomer.

To 400 ml of toluene 1.3 g (0.0116 mole) of potassium t-butoxide and 2.9 ml of a concentrated (90%) solution in hexane of the complex made in accordance with the procedure of Example 1 are added under conditions of stirring and in the absence of oxygen and moisture. Then 1,3-butadiene is added as a gas at a flow rate of about 3.5 liters/min. The temperature rises to about 60°–65° and is maintained in that range throughout the reaction with external cooling. After about 3 hours, the reaction is terminated by the addition of 2 ml of water. The telomeric product is a pale yellow mobile liquid.

EXAMPLE C

Metal-Halogen Exchange.

Under an argon atmosphere, 1 g of p-bromotoluene is dissolved in 50 ml tetrahydrofuran (freshly distilled from lithium aluminum hydride) and the solution is cooled to −78° C. One equivalent consisting of a complex of 50 mole % n-butyllithium and 50 mole % ethyllithium in hexane is added over a 2 minute period with stirring. After 45 minutes, the reaction is quenched with 1 ml anhydrous methanol, followed by removal of the cooling bath. Proton NMR analysis of the resulting solution reveals that 99+% metal-halogen takes place. Also, evidence for the occurrence of alkylation is not detected.

EXAMPLE D

Preparation of DMBA from DMR.

To a room temperature solution of 0.24 moles DMR in 55 ml hexane is added dropwise over a 45 minute period a solution of 0.2 mole of the complex solution of Example 1. After stirring 18 hours, the resulting yellow to orange colored mixture of DMPL is slowly drained into a slurry of 80 ml hexane, 70 ml toluene, and approximately 600 g dry ice (large excess of $CO_2$). The carbonylation is continued at approximately −50° C. or 12 hours, then gradually allowed to warm to room temperature. The tan colored mixture of lithium 2,6-dimethoxybenzoate is slowly quenched by pouring into 400 ml of tap water. The resulting mixture is stirred with a magnetic stirrer for 30 minutes. The pale yellow aqueous layer is separated and decolorized with 1 g activated charcoal. The nearly colorless solution is acidified (Ph~1) with 6 N HCl to cause precipitation of DMBA. The crystalline product is filtered and dried. Then the melting point is determined followed by calculation of percent yield based on moles of the complex of Example 1 used. Analysis of the yield of 2,6-dimethoxyphenyllithium resulting from the metalation step is determined by proton NMR. Using this method, a sample of the mixture resulting from the reaction of complex metalating agent and 1,3-dimethoxybenzene is quenched with deuterium oxide. The proton NMR spectrum reveals greater than 95%±5% deuterium incorporation.

The steps in the foregoing procedure for the production of DMBA according to EXAMPLE D are shown below.

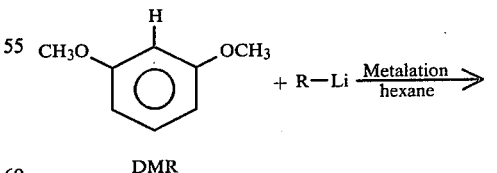

DMR

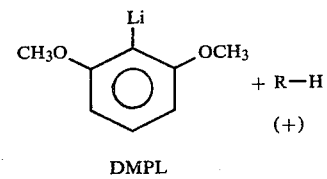

DMPL

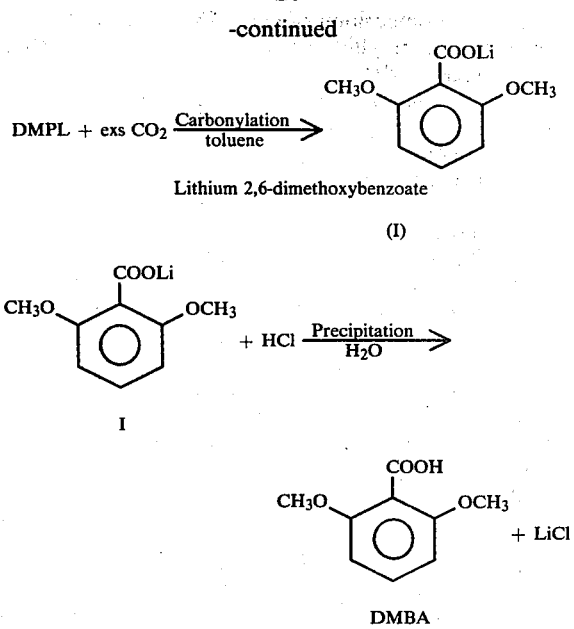

By the process of EXAMPLE D, savings are effected not only through the use of the more economical complexes of n-butyllithium and ethyllithium in place of n-butyllithium, but the complexes appear to be more reactive than n-butyllithium alone.

I claim:

1. In a method of preparing liquid hydrocarbon solutions of complexes of n-butyllithium and ethyllithium in which the ratio of the n-butyllithium to the ethyllithium, on a mole basis, is from about 1:9 to about 9:1, the steps which comprise providing a stirred dispersion of finely divided lithium metal containing a small proportion of sodium metal in a liquid with which the lithium metal is essentially unreactive, discontinuing the stirring and allowing the lithium metal to rise to the top of the mixture, separating out the unreactive liquid and replacing it with a liquid hydrocarbon solvent, gradually adding to said lithium metal dispersion, under conditions of vigorous agitation and in an inert gas atmosphere, a relatively homogeneous mixture of (a) n-butyl chloride or bromide and (b) ethyl chloride or ethyl bromide in predetermined relative proportions to provide the aforesaid solutions containing the complexes in their above-stated mole ratios of the n-butyllithium and ethyllithium, and continuing the reaction at a temperature in the approximate range of about 20° to about 35°, under conditions of stirring, until said reaction is at least substantially completed, filtering and washing the reaction muds with a liquid hydrocarbon solvent for said complexes to produce a final clear hydrocarbon solution of said complexes.

2. The method of claim 1, in which the mole ratio of the n-butyllithium to the ethyllithium in said complexes is equimolar.

3. The method of claim 1, in which the mole ratio of the n-butyllithium to the ethyllithium is about 35 to about 65.

4. The method of claim 1, in which the mole ratio of the n-butyllithium to the ethyllithium is about 25 to about 75.

5. The method of claim 1, in which the hydrocarbon solvent is selected from the group of aliphatic and/or cycloaliphatic hydrocarbon solvents.

6. The method of claim 1, in which the lithium content of said slurry is in excess of the stoichiometric amount thereof in relation to the amounts of n-butyl and ethyl chlorides or bromides.

7. The method of claim 1, in which the weight percentage of said complexes in said aliphatic and/or cycloaliphatic hydrocarbon solvent is such as to produce a dilute solution thereof.

8. The method of claim 7, in which said hydrocarbon solvent is selected from the group of n-hexane and/or cyclohexane.

9. In a method of preparing liquid hydrocarbon solutions of complexes of n-butyllithium and ethyllithium in which the ratio of the n-butyllithium to the ethyllithium, on a mole basis, is from about 1:9 to about 9:1, the steps which comprise providing a stirred dispersion of finely divided lithium metal containing a small proportion of sodium metal in a liquid hydrocarbon selected from the group of aliphatic and cycloaliphatic hydrocarbons with which the lithium metal is essentially unreactive, gradually adding simultaneously to said lithium metal dispersion, under conditions of vigorous agitation and in an inert gas atmosphere, (a) n-butyl chloride or bromide and (b) ethyl chloride or bromide in a predetermined relative proportions to provide the aforesaid solutions containing the complexes in their above-stated mole ratios of the n-butyllithium and ethyllithium, and continuing the reaction at a temperature in the approximate range of about 20° to about 35°, under conditions of stirring, until said reaction is at least substantially completed, and filtering to produce a solution of said complexes in said hydrocarbon solvent.

10. In a method of preparing liquid aliphatic and/or cycloaliphatic hydrocarbon solutions of complexes of n-butyllithium and ethyllithium in which the ratio of the n-butyllithium to the ethyllithium, on a mole basis, is from about 1:9 to about 9:1, the steps of which comprise providing a stirred dispersion of finely divided lithium metal containing a small proportion of sodium metal in a liquid with which the lithium metal is essentially unreactive, discontinuing the stirring and allowing the lithium metal to rise to the top of the mixture, separating out the unreactive liquid and replacing it with a liquid hydrocarbon solvent, gradually adding to said lithium metal dispersion, under conditions of vigorous agitation and in an inert gas atmosphere, a relatively homogeneous mixture of (a) n-butyl chloride or bromide, and (b) ethyl chloride or bromide in predetermined relative proportions to provide the aforesaid solutions containing the complexes in their above-stated mole ratios of the n-butyllithium and ethyllithium, and continuing the reaction at a temperature in the approximate range of about 20° to about 35°, under conditions of stirring, until said reaction is at least substantially completed, filtering and washing the reaction muds with a liquid hydrocarbon solvent for said complexes to produce a final clear hydrocarbon solution of said complexes.

11. The method of claim 10, in which the lithium content of said slurry is in excess of the stoichiometric amount thereof in relation to the amounts of n-butyl and ethyl chlorides or bromides.

12. The method of claim 11, in which the liquid hydrocarbon solvents are selected from the group of n-hexane and cyclohexane.

13. The method of claim 11, in which the mole ratio of the n-butyllithium to the ethyllithium in said complexes is about equimolar.

14. The method of claim 11, in which the mole ratio of the n-butyllithium to the ethyllithium is about 35 to about 65.

15. The method of claim 11, in which the mole ratio of the n-butyllithium to the ethyllithium is about 25 to about 75.

16. The method of claim 11, in which the mole ratios of the n-butyllithium to the ethyllithium in said complexes are selected from the group (a) about equimolar, (b) about 35 to about 65, and (c) about 25 to about 75, and in which the weight percentages of said complexes in said hydrocarbon solvent are such as to produce a dilute solution thereof.

17. A composition comprising a clear solution in a liquid hydrocarbon solvent of a complex of n-butyllithium and ethyllithium in which the ratio, on a mole basis, of the n-butyllithium to the ethyllithium is in the range of about 1:9 to about 9:1.

18. The composition of claim 17, in which the liquid hydrocarbon solvent is selected from the group of aliphatic and cycloaliphatic hydrocarbon solvents.

19. The composition of claim 18, in which the mole ratio of the n-butyllithium to the ethyllithium in said complex is about equimolar.

20. The composition of claim 18, in which the mole ratio of then-butyllithium to the ethyllithium is about 35% to about 65%.

21. The composition of claim 18, in which the mole ratio of the n-butyllithium to the ethyllithium is about 25% to about 75%.

22. The composition of claim 18, in which the aliphatic or cycloaliphatic hydrocarbon is selected from the group of n-hexane and cyclohexane.

23. The composition of claim 18, in which the weight percentage of said complex in said solution is in the range of about 12 to about 25.

24. The composition of claim 23, in which the aliphatic of cycloaliphatic hydrocarbon is selected from the group of n-hexane and cyclohexane.

25. The composition of claims 19, 20 or 21, in which the weight percentage in said solution is in the range of about 12 to about 25.

26. The composition of claims 19, 20 or 21, in which the weight percentage of said complex in said solution is in the range of about 40 to about 72.

27. The composition of claim 19, in which the weight percentage of said complex in said solution is in the range of about 40 to about 99.

* * * * *